(12) United States Patent
Akasapu et al.

(10) Patent No.: US 11,400,068 B2
(45) Date of Patent: Aug. 2, 2022

(54) LIQUID READY-TO-USE FORMULATION OF LEVOTHYROXINE

(71) Applicant: Somerset Therapeutics LLC, Hollywood, FL (US)

(72) Inventors: Prem Sagar Akasapu, Somerset, NJ (US); Rahul Kalhapure, Somerset, NJ (US); Mandar V. Shah, Somerset, NJ (US); Shambhavi Borde, Somerset, NJ (US); Veerappan Subramanian, Somerset, NJ (US); Ilango Subramanian, Somerset, NJ (US)

(73) Assignee: SOMERSET THERAPEUTICS LLC, Hollywood, FL (US)

( * ) Notice: Subject to any disclaimer, the term of this patent is extended or adjusted under 35 U.S.C. 154(b) by 0 days.

(21) Appl. No.: 17/346,500

(22) Filed: Jun. 14, 2021

(65) Prior Publication Data

US 2021/0386699 A1 Dec. 16, 2021

Related U.S. Application Data

(60) Provisional application No. 63/038,196, filed on Jun. 12, 2020.

(51) Int. Cl.
*A61K 31/198* (2006.01)
*A61K 9/00* (2006.01)
*A61K 47/18* (2017.01)

(52) U.S. Cl.
CPC .......... *A61K 31/198* (2013.01); *A61K 9/0019* (2013.01); *A61K 47/183* (2013.01)

(58) Field of Classification Search
CPC .................................................... A61K 31/198
See application file for complete search history.

(56) References Cited

U.S. PATENT DOCUMENTS

2018/0214374 A1* 8/2018 Chandrashekhar .. A61K 31/198

* cited by examiner

*Primary Examiner* — Rei Tsang Shiao
(74) *Attorney, Agent, or Firm* — William D. Hare, Esq.; McNeely, Hare & War, LLP

(57) ABSTRACT

The present invention relates to liquid formulations of levothyroxine or a pharmaceutically acceptable salt thereof intended for parenteral administration, wherein the formulations are devoid of tromethamine. In particular, the invention provides a stable ready-to-use liquid formulation of levothyroxine or a pharmaceutically acceptable salt thereof intended for parenteral administration, wherein the formulation is devoid of tromethamine. The formulations prepared by using the current invention exhibit good physical and chemical stability.

20 Claims, No Drawings

LIQUID READY-TO-USE FORMULATION OF LEVOTHYROXINE

FIELD OF THE INVENTION

Disclosed herein are liquid formulations comprising levothyroxine or a pharmaceutically acceptable salt thereof, particularly ready-to-use liquid formulation comprising levothyroxine sodium which is free of tromethamine. The present invention also relates to a process of preparing such compositions and use thereof.

BACKGROUND OF THE INVENTION

Thyroxine active drugs are known for both therapeutic and prophylactic treatment of thyroid disorders. The thyroid accomplishes its regulation functions by producing the hormones L-triiodothyronine (liothyronine; T3) and L-thyroxine (levothyroxine; T4). Triiodothyronine (T3) and its prohormone thyroxine (T4) are derivatives of the amino acid tyrosine. Levothyroxine is produced by the thyroid gland, and metabolized by peripheral tissues to T3. Thyroid hormones are of widespread biological effect on the growth and development and metabolic processes of many different organs and tissues. The physiological actions of thyroid hormones are produced predominantly by T3, the majority of which (approximately 80%) is derived from T4 by deiodination in peripheral tissues. T3 and/or T4 deficiencies are associated with hypothyroidism, the symptoms of which include tiredness, cold sensitivity, weight gain, goitre, decreased muscle tone, myxedema, decreased motor skills, and cretinism.

Levothyroxine sodium is a synthetic form of thyroxine commonly administered to patients suffering from hypothyroidism in thyroid hormone replacement therapy. Levothyroxine sodium chemically is known as 4-(4-hydroxy-3,5-diiodophenoxy)-3,5-diiodo-L-phenylalanine sodium, and also as L-tyrosine-O-(4-hydroxy-3,5-diiodophenyl)-3,5-diiodo-mono s odium salt. Levothyroxine sodium has a molecular weight of approximately 798.85 and the following chemical structure:

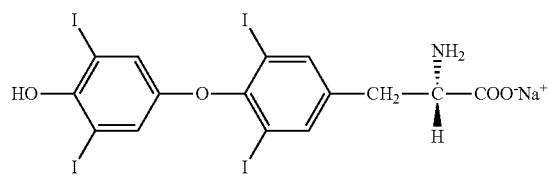

Levothyroxine has a narrow therapeutic index and overtreatment or under-treatment may affect growth and development, cardiovascular function, bone metabolism, reproductive function, cognitive function, emotional state, gastrointestinal function, and glucose and lipid metabolism.

Levothyroxine sodium is available in the form of capsules, tablets and parenteral dosage forms. Levothyroxine sodium for injection is available as sterile lyophilized product for parenteral administration containing 100 µg/vial, 200 µg/vial and 500 µg/vial.

Levothyroxine sodium is quite unstable, hygroscopic and degrades rapidly when subjected to high humidity, light or high temperature. Due to this instability, levothyroxine injectable formulations are used in the form of lyophilized formulations that are dissolved in 0.9% sodium chloride Injection immediately before injection.

Conventional formulations of levothyroxine sodium for injection are preservative-free lyophilized powders containing synthetic crystalline levothyroxine sodium, mannitol, dibasic sodium phosphate, and sodium hydroxide. These conventional formulations typically contain 10 mg mannitol, 700 µg of dibasic sodium phosphate and 100 µg or 200 µg or 500 µg of levothyroxine sodium. Administration of the conventional formulation involves reconstitution of the lyophilized powder in 5 mL of 0.9% sodium chloride injection, to provide injectable solutions having levothyroxine sodium concentrations of 20 µg/mL, 40 µg/mL or 100 µg/mL. However, the reconstituted solutions have a limited stability, and must be used within 4 hours of reconstitution. In addition, the reconstitution process may have the potential chances for contamination and thereby compromising patient safety.

A ready-to-use (RTU) levothyroxine sodium injection for intravenous administration has been developed by Fresenius Kabi USA LLC and approved by United States Food and Administration United States (USFDA) for the treatment of myxedema coma. This ready-to-use solution is available as: 100 µg per 5 mL (20 µg per mL), 200 µg per 5 mL (40 µg per mL), and 500 µg per 5 mL (100 µg per mL). Each mL of levothyroxine sodium injection also contains 10 mg tromethamine, USP; 0.14 mg sodium iodide, USP; 6.48 mg sodium chloride, USP; and water for injection (WFI), USP, sodium hydroxide, NF and/or hydrochloric acid, USP may have been added for pH adjustment (9.5-10.8).

In the field of injectable preparations, liquid levothyroxine sodium injection for intravenous administration have already been described in scientific and patent literature.

U.S. Pat. No. 9,006,289 B2 discloses lyophilized compositions comprising of levothyroxine sodium, a phosphate buffer and mannitol.

U.S. Pat. No. 9,782,376 B1 and its equivalents disclose liquid parenteral pharmaceutical formulation comprising levothyroxine or a pharmaceutically acceptable salt thereof, tromethamine sodium iodide and water. The '376 Patent explains that tromethamine is added as a buffer with a range of about 7 to about 9 but that it offers an addition advantage of providing a stabilizing effect on levothyroxine by a mechanism unrelated to buffering of the formulation.

U.S. Patent Publication No. US 20180214374 A1 discloses liquid parenteral pharmaceutical formulations of levothyroxine comprising levothyroxine or a pharmaceutically acceptable salt thereof, stabilizing agents and/or solubilizing agents, buffering agents and one or more solvents. The stabilizing agents used in the formulation include sodium iodide, potassium iodide and solubilizing agents such as cyclodextrins.

Due to instability in aqueous solutions, levothyroxine undergoes degradation to form 3,3',5-triiodothyronine (T3), 3,5-diiodothyronine (T2), 3,3',5,5'-tetraiodothyroacetic acid (TTAA4), 3,3',5-triiodothyroacetic acid (TTAA3), and 3,5-diiodothyroacetic acid. Aqueous solutions of levothyroxine sodium have been shown to be more stable at basic pH than at acidic pH, but significant degradation of levothyroxine sodium also has been shown to occur at basic pH. Therefore, preparing a stable liquid formulation of levothyroxine, especially aqueous formulations with minimal degradation of drug is always challenging for a formulator to prepare.

Thus, the inventors have determined that there is an enduring need to develop levothyroxine formulation that provides an alternative to existing formulations. The present inventors of the present invention have developed liquid formulations of levothyroxine or a pharmaceutically acceptable salt thereof intended for parenteral administration, wherein the formulations are devoid of tromethamine. In particular, the inventors of the present invention have developed a ready-to-use liquid formulation of levothyroxine sodium, wherein the formulation is devoid of tromethamine. The formulations prepared by using the current invention exhibits good physical and chemical stability.

SUMMARY OF THE INVENTION

The present invention provides liquid formulations of levothyroxine or a pharmaceutically acceptable salt thereof intended for parenteral administration. In particular, the invention provides stable ready-to-use liquid formulations of levothyroxine or a pharmaceutically acceptable salt thereof intended for parenteral administration, wherein the formulations are devoid of tromethamine.

In one general aspect, there is provided stable ready-to-use liquid formulations of levothyroxine or a pharmaceutically acceptable salt thereof, wherein the formulations are devoid of tromethamine.

In one general aspect, there is provided a stable ready-to-use liquid formulation comprising levothyroxine or a pharmaceutically acceptable salt in a concentration of about 1 µg/mL to about 500 µg/mL, wherein the formulation is devoid of tromethamine.

In one general aspect, there is provided a stable ready-to-use liquid formulation comprising levothyroxine or a pharmaceutically acceptable salt in a concentration of about 10 µg/mL to about 500 µg/mL, wherein the formulation is devoid of tromethamine.

In one general aspect, there is provided a stable ready-to-use liquid formulation comprising levothyroxine or a pharmaceutically acceptable salt in a concentration of about 20 µg/mL to about 100 µg/mL, wherein the formulation is devoid of tromethamine.

In one general aspect, there is provided a stable ready-to-use liquid formulation comprising levothyroxine or a pharmaceutically acceptable salt in a concentration of about 20 µg/mL to about 100 µg/mL and one or more pharmaceutically acceptable excipients, wherein the formulation is devoid of tromethamine.

In one general aspect, there is provided a stable ready-to-use liquid formulation comprising levothyroxine or a pharmaceutically acceptable salt in a concentration of about 20 µg/mL to about 100 µg/mL and one or more pharmaceutically acceptable excipients selected from buffers or buffering agents, chelating agents, stabilizing agents, tonicity agents, pH adjusting agents, antioxidants, preservatives and water, wherein the formulation is devoid of tromethamine.

In one general aspect, there is provided a stable ready-to-use liquid formulation comprising levothyroxine or a pharmaceutically acceptable salt in a concentration of about 20 µg/mL to about 100 µg/mL, buffers, stabilizing agents, tonicity agents and water, wherein the formulation is devoid of tromethamine.

In one general aspect, there is provided a stable ready-to-use liquid formulation comprising levothyroxine sodium in a concentration of about 20 µg/mL to about 100 µg/mL, buffers, stabilizing agent, tonicity agents and water, wherein the formulation is devoid of tromethamine.

In one general aspect, there is provided a stable ready-to-use liquid formulation comprising levothyroxine sodium in a concentration of about 20 µg/mL to about 100 µg/mL, buffers in a concentration of about 1 mg/mL to about 50 mg/mL, stabilizing agent in a concentration of about 10 µg/mL to about 300 µg/mL, tonicity agents and water, wherein the formulation is devoid of tromethamine.

In one general aspect, there is provided a stable ready-to-use liquid formulation comprising levothyroxine sodium in a concentration of about 20 µg/mL to about 100 µg/mL and buffers selected from amino acids, (3-(cyclohexylamino)-2-hydroxy-1-propanesulfonic acid sodium salt), 2-amino-2-methyl-1-propanol, 3-(cyclohexylamino)-1-propanesulfonic acid, monothioglycerol, N,N,N',N'-tetrakis(2-hydroxyethyl)ethylenediamine (THEED), ethylenediamine, monoethanolamine, diethanolamine, triethanolamine, triisopropanolamine, 1-amino-2-propanol, 2-amino-2-methyl-1,3-propanediol, 2-dimethylamino-2-methyl-1-propanediol, 2-amino-2-ethylpropanol, citrate, glutamate, bicarbonate, tartrate, benzoate, lactate, gluconate, acetate, meglumine, borate and phosphate alone or in combination thereof, wherein the formulation is devoid of tromethamine.

In one general aspect, there is provided a stable ready-to-use liquid formulation comprising levothyroxine sodium in a concentration of about 20 µg/mL to about 100 µg/mL and stabilizing agent selected from sodium iodide, potassium iodide, cyclodextrins and the like, wherein the formulation is devoid of tromethamine.

In one general aspect, there is provided a stable ready-to-use liquid formulation comprising levothyroxine sodium in a concentration of about 20 µg/mL to about 100 µg/mL, buffers in a concentration of about 1 mg/mL to about 20 mg/mL and stabilizing agent in a concentration of about 0.01 mg/mL to about 5 mg/mL, wherein the formulation is devoid of tromethamine.

In one general aspect, there is provided a stable ready-to-use liquid formulation comprising levothyroxine sodium in a concentration of about 20 µg/mL to about 100 µg/mL, buffers selected from amino acids, (3-(cyclohexylamino)-2-hydroxy-1-propanesulfonic acid sodium salt), 2-amino-2-methyl-1-propanol, 3-(cyclohexylamino)-1-propanesulfonic acid, monothioglycerol, N,N,N',N'-tetrakis(2-hydroxyethyl)ethylenediamine (THEED), ethylenediamine, monoethanolamine, diethanolamine, triethanolamine, triisopropanolamine, 1-amino-2-propanol, 2-amino-2-methyl-1,3-propanediol, 2-dimethylamino-2-methyl-1-propanediol, 2-amino-2-ethylpropanol, citrate, glutamate, bicarbonate, tartrate, benzoate, lactate, gluconate, acetate, meglumine, borate and phosphate alone or in combination thereof, stabilizing agent selected from sodium iodide, potassium iodide, cyclodextrins and the like, wherein the formulation is devoid of tromethamine.

In one general aspect, there is provided a stable ready-to-use liquid formulation comprising levothyroxine sodium in a concentration of about 20 µg/mL, about 40 µg/mL or about 100 µg/mL, buffers selected from amino acids, (3-(cyclohexylamino)-2-hydroxy-1-propanesulfonic acid sodium salt), 2-amino-2-methyl-1-propanol, 3-(cyclohexylamino)-1-propanesulfonic acid, monothioglycerol, N,N,N',N'-tetrakis(2-hydroxyethyl)ethylenediamine (THEED), ethylenediamine, monoethanolamine, diethanolamine, triethanolamine, triisopropanolamine, 1-amino-2-propanol, 2-amino-2-methyl-1,3-propanediol, 2-dimethylamino-2-methyl-1-propanediol, 2-amino-2-ethylpropanol, citrate, glutamate, bicarbonate, tartrate, benzoate, lactate, gluconate, acetate, meglumine, borate and phosphate alone or in combination thereof, stabilizing agent selected from sodium iodide, potassium iodide, cyclodextrins and the like in a concentration of about 0.01 mg/mL to about 5 mg/mL, wherein the formulation is devoid of tromethamine.

In one general aspect, there is provided a stable ready-to-use liquid formulation comprising levothyroxine sodium in a concentration of about 20 µg/mL to about 100 µg/mL, amino acids selected from glycine, lysine and histidine and stabilizing agent selected from sodium iodide, potassium iodide, cyclodextrins and the like, wherein the formulation is devoid of tromethamine.

In one general aspect, there is provided a stable ready-to-use liquid formulation comprising levothyroxine sodium in a concentration of about 20 μg/mL to about 100 μg/mL, amino acids selected from glycine, lysine and histidine, and stabilizing agents selected from sodium iodide, potassium iodide, cyclodextrins and the like, wherein the formulation is devoid of tromethamine and further comprises of isotonicity agent selected from sodium chloride and glycerol, pH adjusting agents selected from sodium hydroxide or hydrochloride and water.

In one general aspect, there is provided a stable ready-to-use liquid formulation comprising levothyroxine sodium in a concentration of about 20 μg/mL to about 100 μg/mL, glycine, sodium iodide, wherein the formulation is devoid of tromethamine.

In one general aspect, there is provided a stable ready-to-use liquid formulation comprising levothyroxine sodium in a concentration of about 20 μg/mL to about 100 μg/mL, glycine, sodium iodide, wherein the formulation is devoid of tromethamine and further comprises of isotonicity agent selected from sodium chloride and glycerol, pH adjusting agents selected from sodium hydroxide or hydrochloride and water.

In one general aspect, there is provided a stable ready-to-use liquid formulation comprising levothyroxine sodium in a concentration of about 20 μg/mL to about 100 μg/mL, glycine, sodium iodide, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, glycine, sodium iodide, wherein the formulation is devoid of tromethamine and further comprises of glycerol, sodium hydroxide or hydrochloride and water.

In one general aspect, there is provided a stable ready-to-use liquid formulation comprising levothyroxine sodium in a concentration of about 20 μg/mL to about 100 μg/mL, lysine, sodium iodide, wherein the formulation is devoid of tromethamine.

In one general aspect, there is provided a stable ready-to-use liquid formulation comprising levothyroxine sodium in a concentration of about 20 μg/mL to about 100 μg/mL, lysine, sodium iodide, wherein the formulation is devoid of tromethamine and further comprises an isotonicity agent selected from sodium chloride and glycerol, pH adjusting agents selected from sodium hydroxide or hydrochloride, and water.

In one general aspect, there is provided a stable ready-to-use liquid formulation comprising levothyroxine sodium in a concentration of about 20 μg/mL to about 100 μg/mL, lysine, sodium iodide, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, lysine, sodium iodide, wherein the formulation is devoid of tromethamine and further comprises of glycerol, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, 2-amino-2-methyl-1-propanol and monothioglycerol, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, diethanolamine and 2-amino-2-methyl-1-propanol, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, 2-amino-2-methyl-1-propanol, and N, N, N', N'-Tetrakis(2-hydroxyethyl) ethylenediamine, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, triethanolamine and ethanolamine, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, triisopropanolamine and 1-amino-2-propanol, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, diisopropanolamine and 1-amino-2-propanol, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, ethylenediamine and monothioglycerol, wherein the formulation is devoid of tromethamine and further comprises of sodium chloride, sodium hydroxide or hydrochloride and water.

In one general aspect, there is provided a stable ready-to-use liquid formulation comprising levothyroxine sodium in a concentration of about 20 μg/mL to about 100 μg/mL, sodium iodide, ethylenediamine and N, N, N', N'-Tetrakis(2-hydroxyethyl) ethylenediamine, wherein the formulation is devoid of tromethamine and further comprises of sodium chloride, sodium hydroxide or hydrochloride and water.

In one general aspect, there is provided a process for preparation of a stable ready-to-use liquid formulation comprising levothyroxine or a pharmaceutically acceptable salt and a unit package formulation of the same, wherein the formulation is devoid of tromethamine.

In one general aspect, there is provided a process for preparation of a stable ready-to-use liquid formulation comprising levothyroxine or a pharmaceutically acceptable salt, wherein the formulation is devoid of tromethamine and filled in a vial, an ampoule, a bag, a bottle, a cartridge, or a syringe.

In one general aspect, there is provided a process for preparation of a stable ready-to-use liquid formulation of levothyroxine or a pharmaceutically acceptable salt and one or more pharmaceutically acceptable excipients, which is devoid of tromethamine.

In another general aspect, there is provided a ready-to-use liquid formulation of levothyroxine or a pharmaceutically acceptable salt, wherein the formulation is devoid of tromethamine and characterized in that the formulation retains at least 90% w/w of the potency of levothyroxine when stored at 25° C. and 60% relative humidity or at 40° C. and 75% relative humidity for 3 months.

In another general aspect, there is provided a process for preparing a liquid formulation of levothyroxine or a pharmaceutically acceptable salt, wherein the obtained formulation is aseptically distributed into single dose or multidose containers.

In another general aspect, there is provided a ready-to-use liquid formulation of levothyroxine or a pharmaceutically acceptable salt, wherein the obtained formulation exhibits good stability throughout the shelf life as the impurities observed are well below the specified limits.

DETAILED DESCRIPTION OF THE INVENTION

The invention provides a stable ready-to-use liquid formulations of levothyroxine or a pharmaceutically acceptable salt thereof. In particular, the invention provides a stable ready-to-use liquid formulations of levothyroxine or a pharmaceutically acceptable salt thereof intended for parenteral administration, wherein the formulations are devoid of tromethamine.

The term "Levothyroxine" used throughout the specification refers to not only levothyroxine per se, but also its other pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. The formulations of the present invention preferably comprise levothyroxine sodium.

The term "formulation" as used herein, is interchangeable with composition and refers to preparations comprising levothyroxine or a pharmaceutically acceptable salt; in a form suitable for administration to a mammal.

The term "ready-to-use" as used herein, refers to a liquid for parenteral administration that is not obtained by reconstituting a lyophilized product. The liquid ready-to-use solutions as per this invention are not diluted with any diluent before administration.

The term "stable formulation" as used herein, refers to any preparation of levothyroxine or pharmaceutically acceptable salts thereof having sufficient physical and chemical stability to allow storage at a convenient temperature, such as between about 0° C. and about 50° C., for a commercially reasonable period of time. The term "physical stability" refers to maintenance of colour, dissolved oxygen level, head space oxygen level, and particulate matter. The term "chemical stability" relates to formation of drug-related impurities in terms of total impurity, single maximum individual impurity and maximum individual unknown impurity. For the purpose of the present invention chemical stability also includes maintenance of pH of the finished formulation. For pharmaceutical products, stability is required for commercially relevant times after manufacturing, such as for about 6, 12, 18, 24 or 36 months, during which a product is kept in its original packaging under specified storage condition.

The term "shelf life" refers to the amount of time the formulations may be stored without loss of potency and/or dissolution profile. Preferably, the shelf life refers to the amount of time the formulations may be stored without a loss of more than 2%, 5%, 8% or 10% of the potency and/or dissolution.

The term "about" as used herein, is used where measurements are understood to vary due to measurement issues or variability in populations, such as results of clinical studies. The scope of such terms will depend on the context of the element at issue and the understanding of those skilled in the art. In the absence of such guidance in the art, through relevant teachings or examples, the term "about" should be understood as meaning +/−10% of the indicated value(s).

The stable ready-to-use liquid levothyroxine formulation refers to a formulation that retains at least about 90%, or about least about 95%, or at least about 96%, or at least about 98%, of the labelled concentration of levothyroxine or pharmaceutically acceptable salt thereof after storage under typical and/or accelerated conditions.

The concentration of levothyroxine or a pharmaceutically acceptable salt in the formulation is about 1 µg/mL to about 500 µg/mL.

The formulations include levothyroxine or a pharmaceutically acceptable salt suitable for parenteral administration and one or more pharmaceutically acceptable excipients selected from buffers or buffering agents, chelating agent, antioxidant, stabilizing agents, tonicity agents, pH adjusting agents, preservatives and solvent, wherein the formulation is devoid of tromethamine.

Exemplary buffers include, but are not limited to amino acids, (3-(cyclohexylamino)-2-hydroxy-1-propanesulfonic acid sodium salt), 2-amino-2-methyl-1-propanol, 3-(cyclohexylamino)-1-propanesulfonic acid, monothioglycerol, N,N,N',N'-tetrakis(2-hydroxyethyl)ethylenediamine (THEED), ethylenediamine, monoethanolamine, diethanolamine, triethanolamine, triisopropanolamine, 1-amino-2-propanol, 2-amino-2-methyl-1,3-propanediol, 2-dimethylamino-2-methyl-1-propanediol, 2-amino-2-ethylpropanol, citrate, glutamate, bicarbonate, tartrate, benzoate, lactate, gluconate, acetate, meglumine, borate, ammonium and phosphate alone or in combination thereof. The amino acids include but are not limited to glycine, lysine and histidine. If lysine is the buffer, it may be used in an amount of 0.1 mg to 7.0 mg per ml of the composition or individual amounts and ranges within such as 1.0 mg/ml to 2.0 mg/ml, 2.0 mg/ml to 3.0 mg/ml, 3.0 mg/ml to 4.0 mg/ml, 4.0 mg/ml to 5.0 mg/ml, 5.0 mg/ml to 6.0 mg/ml, 6.0 mg/ml to 7.0 mg/ml, or about 1.1 mg/ml, about 1.2 mg/ml, about 1.3 mg/ml, about 1.4 mg/ml, about 1.5 mg/ml, 1.6 mg/ml, 1.7 mg/ml, 1.8 mg/ml, 1.9 mg/ml, or about 1.15 mg/ml, about 1.25 mg/ml, about 1.35 mg/ml, about 1.45 mg/ml, about 1.55 mg/ml, about 1.65 mg/ml, about 1.75 mg/ml, 1.85 mg/ml, about 1.95 mg/ml. Individual amounts include 1.41 mg/ml, 1.42 mg/ml, 1.43 mg/ml, 1.44 mg/ml, 1.45 mg/ml, 1.46 mg/ml, 1.47 mg/ml, 1.48 mg/ml, 1.49 mg/ml.

The stabilizing agent used in liquid formulations is to stabilize levothyroxine or pharmaceutically acceptable salts thereof and is selected from sodium iodide, potassium iodide, cyclodextrins and the like. The concentration of stabilizing agent used in the liquid formulations may be of about 0.01 mg/mL to about 5 mg/mL.

The pH-adjusting agent(s) are used in liquid formulations to adjust the pH to a desirable range. Exemplary pH-adjusting agents are well known by those skilled in the art and include sodium hydroxide, sodium carbonate, sodium bicarbonate, potassium hydroxide, ammonium carbonate, hydrochloric acid, citric acid, lactic acid, phosphoric acid, sodium phosphate, sulfuric acid and the like. While not intending to limit the scope of the invention in any way, certain formulations disclosed herein may have a pH of about 9.0 or more, preferably in the range of about 8.0 to about 12.0.

The tonicity agents are used in liquid formulations to adjust the composition of the formulation to be within the desired isotonic range. Exemplary tonicity agents include, but are not limited to sodium chloride, potassium chloride, dextrose, glycerol, and mannitol. The tonicity agents are in the amount of about 0.01% to 20% by weight.

The preservatives in the liquid formulations are used to inhibit the microbial growth. Suitable preservatives include, but are not limited to, hydrogen peroxide; sorbic acid; biquanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal and the like.

Chelating agents are used in the liquid formulations to enhance preservative effectiveness by forming stable water-soluble complexes (chelates) with alkaline earth and heavy metal ions. Exemplary chelating agents include, but are not limited to, ethylenediaminetetraacetic acid (EDTA), or salts thereof. The chelating agent typically is present in an amount from about 0.001-0.1% by weight. In the case of EDTA, the chelating agent is preferably present at a concentration of about 0.025% by weight.

The liquid formulations of the present invention may also contain one or more anti-oxidants such as sodium sulfite, sodium bisulfite, sodium metabisulfite, sodium thiosulphate, sodium formaldehyde sulfoxylate, citric acid, tocopherol, butylated hydroxy anisole, butylated hydroxy toluene, monothioglycerol, dithioerythreitol, ascorbic acid, sodium ascorbate, propyl gallate, acetyl cysteine and thioglycolic acid.

The formulations can be prepared by using any suitable technique, many of which are known to those skilled in the art and can be combined in any order.

The formulations disclosed herein can consist of or consist essentially of the listed ingredients. If the formulations consist essentially of the listed ingredients, other ingredients may be present so long as they do not affect the stability of the levothyroxine in the formulation, for example, as measured by assay.

It is to be understood that the above description is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

Example 1: Levothyroxine Sodium Injection Composition with Glycine and Glycerol

| Sr. No | Ingredient | Quantity/mL |
|---|---|---|
| 1 | Levothyroxine sodium | 20 μg-100 μg |
| 2 | Sodium Iodide | 0.01 mg-1.0 mg |
| 3 | Glycine | 0.075 mg-9.0 mg |
| 4 | Glycerol | 1.0 mg-200 mg |
| 5 | NaOH and/or HCl | q.s. to adjust pH 9.0 to 11.0 |
| 6 | Water | 1 mL |

Manufacturing Process: The manufacturing process has the following steps:
1. Dissolve the weighed quantity of glycine and glycerol in water using a stirrer.
2. Add the required quantity of sodium iodide and stir until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with $N_2$ and stopper.

Example 2: Levothyroxine Sodium Injection Composition with Lysine and Glycerol

| Sr. No | Ingredient | Quantity/mL |
|---|---|---|
| 1 | Levothyroxine sodium | 20 μg-100 μg |
| 2 | Sodium iodide | 0.14 mg |
| 3 | Lysine | 0.1 mg-7.0 mg |
| 4 | Glycerol | 1.0 mg-200 mg |
| 5 | NaOH and/or HCl | q.s. to adjust pH 9.0 to 11.0 |
| 6 | Water | 1 mL |

Manufacturing Process: The manufacturing process has the following steps:
1. Dissolve the weighed quantity of lysine and glycerol in water using a stirrer.
2. Add the required quantity of sodium iodide and stir until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with $N_2$ and stopper.

Example 3: Levothyroxine Sodium Injection Composition with Diethanolamine and 2-amino-2-methyl-1-propanol

| Sr. No | Ingredient | Quantity/mL |
|---|---|---|
| 1 | Levothyroxine sodium | 20 μg-100 μg |
| 2 | Sodium Iodide | 0.14 mg |
| 3 | Diethanolamine | 4.34 mg |
| 4 | 2-amino-2-methyl-1-propanol | 0.1 mg-12.0 mg |

| Sr. No | Ingredient | Quantity/mL |
|---|---|---|
| 5 | Sodium Chloride | 0.1 mg-10.0 mg |
| 6 | NaOH and/or HCl | q.s. to adjust pH 9.0 to 11.0 |
| 7 | Water | 1 mL |

Manufacturing Process: The manufacturing process has the following steps:
1. Dissolve the weighed quantity of diethanolamine and 2-amino-2-methyl-1-propanol in water using a stirrer.
2. Add the required quantity of sodium iodide and then sodium chloride under stirring until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with $N_2$ and stopper.

Example 4: Levothyroxine Sodium Injection Composition with 2-amino-2-methyl-1-Propanol and Monothioglycerol

| Sr. No | Ingredient | Quantity/mL |
|---|---|---|
| 1 | Levothyroxine sodium | 20 µg-100 µg |
| 2 | Sodium Iodide | 0.14 mg |
| 3 | 2-amino-2-methyl-1-propanol | 0.1 mg-12.0 mg |
| 4 | Monothioglycerol | 0.1 mg-12.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve the weighed quantity of 2-amino-2-methyl-1-propanol and monothioglycerol in water using a stirrer.
2. Add the required quantity of sodium iodide and then sodium chloride under stirring until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with $N_2$ and stopper.

Example 5: Levothyroxine Sodium Injection Composition with 2-amino-2-methyl-1-propanol and N, N, N', N'-Tetrakis(2-hydroxyethyl) ethylenediamine

| Sr. No | Ingredient | Quantity/mL |
|---|---|---|
| 1 | Levothyroxine sodium | 20 µg-100 µg |
| 2 | Sodium Iodide | 0.14 mg |
| 3 | 2-amino-2-methyl-1-propanol | 0.1 mg-12.0 mg |
| 4 | N,N,N',N'-Tetrakis(2-hydroxyethyl) ethylenediamine | 0.1 mg-30.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve the weighed quantity of 2-amino-2-methyl-1-propanol and N, N, N', N'-Tetrakis(2-hydroxyethyl) ethylenediamine in water using a stirrer.
2. Add the required quantity of sodium iodide and then sodium chloride under stirring until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with nitrogen and stopper.

Example 6: Levothyroxine Sodium Injection Composition with Triethanolamine and Ethanolamine

| Sr. No | Ingredient | Quantity/mL |
|---|---|---|
| 1 | Levothyroxine sodium | 20 µg-100 µg |
| 2 | Sodium Iodide | 0.14 mg |
| 3 | Triethanolamine | 0.1 mg-15.0 mg |
| 4 | Ethanolamine | 0.1 mg-15.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve sodium chloride in water under nitrogen.
2. Add the required quantity of sodium iodide and stir until it dissolves.
3. Add the required quantity of triethanolamine and ethanolamine, one material at a time and stir till its dissolution.
4. Measure the pH and if necessary adjust the pH to 9.0 to 11.0 with NaOH and/or HCl.
5. Add accurately weighed quantity of levothyroxine sodium under stirring to dissolve and make up the desired volume.
6. Transfer the product into appropriate sterile containers, measure the pH, purge with nitrogen and stopper.

Example 7: Levothyroxine Sodium Injection Composition with Triisopropanolamine and 1-amino-2-propanol

| Sr. No | Ingredient | Quantity/mL |
|---|---|---|
| 1 | Levothyroxine sodium | 20 µg-100 µg |
| 2 | Sodium Iodide | 0.14 mg |
| 3 | Triisopropanolamine | 0.1 mg-15.0 mg |
| 4 | 1-amino-2-propanol | 0.1 mg-15.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve sodium chloride in water under nitrogen.
2. Add the required quantity of sodium iodide and stir until it dissolves.
3. Add the required quantity of triisopropanolamine and 1-amino-2-propanol, one material at a time and stir till its dissolution.
4. Measure the pH and if necessary adjust the pH to 9.0 to 11.0 with NaOH and/or HCl.
5. Add accurately weighed quantity of levothyroxine sodium under stirring to dissolve and make up the desired volume.
6. Transfer the product into appropriate sterile containers, measure the pH, purge with nitrogen and stopper.

Example 8: Levothyroxine Sodium Injection Composition with Diisopropanolamine and 1-amino-2-propanol

| Sr. No | Ingredient | Quantity/mL |
|---|---|---|
| 1 | Levothyroxine sodium | 20 µg-100 µg |
| 2 | Sodium Iodide | 0.14 mg |
| 3 | Diisopropanolamine | 0.1 mg-15.0 mg |
| 4 | 1-amino-2-propanol | 0.1 mg-15.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve sodium chloride in water under nitrogen.
2. Add the required quantity of sodium iodide and stir until it dissolves.
3. Add the required quantity of diisopropanolamine and 1-amino-2-propanol, one material at a time and stir till its dissolution.
4. Measure the pH and if necessary adjust the pH to 9.0 to 11.0 with NaOH and/or HCl.
5. Add accurately weighed quantity of levothyroxine sodium under stirring to dissolve and make up the desired volume.
6. Transfer the product into appropriate sterile containers, measure the pH, purge with nitrogen and stopper.

Example 9: Levothyroxine Sodium Injection Composition with Ethylenediamine and Monothioglycerol

| Sr. No | Ingredient | Quantity/mL |
|---|---|---|
| 1 | Levothyroxine sodium | 20 µg-100 µg |
| 2 | Sodium Iodide | 0.14 mg |
| 3 | Ethylenediamine | 0.1 mg-12.0 mg |
| 4 | Monothioglycerol | 0.1 mg-12.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve sodium chloride in water under nitrogen.
2. Add the required quantity of sodium iodide and stir until it dissolves.
3. Add the required quantity of ethylenediamine and monothioglycerol, one material at a time and stir till its dissolution.
4. Measure the pH and if necessary adjust the pH to 9.0 to 11.0 with NaOH and/or HCl.
5. Add accurately weighed quantity of levothyroxine sodium under stirring to dissolve and make up the desired volume.
6. Transfer the product into appropriate sterile containers, measure the pH, purge with nitrogen and stopper.

Example 10: Levothyroxine Sodium Injection Composition with Ethylenediamine and N, N, N', N'-Tetrakis(2-hydroxyethyl) ethylenediamine

| Sr. No | Ingredient | Quantity/mL |
|---|---|---|
| 1 | Levothyroxine sodium | 20 µg-100 µg |
| 2 | Sodium Iodide | 0.14 mg |
| 3 | Ethylenediamine | 0.1 mg-12.0 mg |
| 4 | N,N,N',N'-Tetrakis(2-hydroxyethyl) ethylenediamine | 0.1 mg-30.0 mg |
| 5 | Sodium Chloride | 6.48 mg |
| 6 | NaOH and/or HCl | q.s. to adjust pH 9.0 to 11.0 |
| 7 | Water | 1 mL |

Manufacturing Process: The manufacturing process has the following steps:
1. Dissolve sodium chloride in water under nitrogen.
2. Add the required quantity of sodium iodide and stir until it dissolves.
3. Add the required quantity of ethylenediamine and N, N, N', N'-Tetrakis(2-hydroxyethyl) ethylenediamine, one material at a time and stir till its dissolution.
4. Measure the pH and if necessary adjust the pH to 9.0 to 11.0 with NaOH and/or HCl.
5. Add accurately weighed quantity of levothyroxine sodium under stirring to dissolve and make up the desired volume.
6. Transfer the product into appropriate sterile containers, measure the pH, purge with nitrogen and stopper.

Example 11: Levothyroxine Sodium Injection Composition with Glycine and Sodium Chloride

| Sr. No | Ingredient | Quantity/mL |
|---|---|---|
| 1 | Levothyroxine sodium | 20 µg-100 µg |
| 2 | Sodium Iodide | 0.1 mg-1.0 mg |
| 3 | Glycine | 0.075 mg-9.0 mg |
| 4 | Sodium chloride | 6.48 mg |
| 5 | NaOH and/or HCl | q.s. to adjust pH 9.0 to 11.0 |
| 6 | Water | 1 mL |

Manufacturing Process: The manufacturing process has the following steps:
1. Dissolve the weighed quantity of glycine and sodium chloride in water using a stirrer.
2. Add required quantity of sodium iodide and stir until it dissolves.
3. Measure the pH and if necessary adjust the pH to 9.0 to 11.0.
4. Add accurately weighed quantity of levothyroxine sodium under stirring to dissolve and make up the desired volume.

5. Transfer the product into appropriate sterile containers, measure the pH, purge with $N_2$ and stopper.

Example 12: Levothyroxine Sodium Injection Composition with Lysine and Sodium Chloride

| Sr. No | Ingredient | Quantity/mL |
|---|---|---|
| 1 | Levothyroxine sodium | 10 µg-1000 µg |
| 2 | Sodium iodide | 0.14 mg |
| 3 | Lysine | 1.46 mg |
| 4 | Sodium Chloride | 8.5 mg |
| 5 | NaOH and/or HCl | q.s. to adjust pH 6.0 to 9.0 |
| 6 | Water | 1 mL |

Manufacturing Process: The manufacturing process has the following steps:
1. Dissolve the weighed quantity of lysine and sodium chloride in water using a stirrer.
2. Add the required quantity of sodium iodide and stir until it dissolves.
3. Measure the pH and if necessary adjust the pH to 9.0 to 11.0 with NaOH and/or HCl.
4. Add accurately weighed quantity of levothyroxine sodium under stirring to dissolve and make up the desired volume.
5. Transfer the product into appropriate sterile containers, measure the pH, purge with $N_2$ and stopper.

Example 13: Levothyroxine Sodium Injection Composition with Lysine and Sulfobutylether-β-cyclodextrin

| Sr. No | Ingredient | Quantity/mL |
|---|---|---|
| 1 | Levothyroxine sodium | 10 µg-1000 µg |
| 2 | Sodium iodide | 0.14 mg |
| 3 | Lysine | 1.46 mg |
| 4 | Sulfobutylether-β-cyclodextrin | 80 mg |
| 5 | Sodium Chloride | 6.48 mg |
| 6 | NaOH and/or HCl | q.s. to adjust pH 6.0 to 9.0 |
| 7 | Water | 1 mL |

Manufacturing Process: The manufacturing process has the following steps:
1. Add weighed quantity of sulfobutylether-β-cyclodextrin (SBCD) in 80% of target volume of milli-Q water and start nitrogen purging while stirring.
2. After complete dissolution of SBCD, add accurately weighed quantity of levothyroxine sodium and ensure its dissolution.
3. Add lysine and dissolve it.
4. Dissolve other formulation ingredients in following order: i) sodium iodide and ii) sodium chloride.
5. Measure the pH. If necessary, adjust the pH between 6.0 to 9.0 with NaOH and/or HCl.
6. QS to desired volume using a volumetric flask and stir for 10 minutes to ensure its homogeneity.
7. Transfer the product to pyrex glass bottle.
8. Measure the pH, purge with $N_2$ and stopper the bottle.

The formulations prepared according to the invention as described in the above examples were tested for stability storage under typical and/or accelerated conditions. The stability conditions can include 25° C./60% relative humidity, 40° C./75% relative humidity, 25° C./40% relative humidity, and/or 40° C./25% relative humidity. The analytical results of the formulations are summarized in Table 1 and 2.

TABLE 1

| Formulation Examples | pH and Assay | Storage Temperatures | | | | | | | | | |
|---|---|---|---|---|---|---|---|---|---|---|---|
| | | 25° C. | | | | | 40° C. | | | | |
| | | Initial | 1-week | 2-week | 3-week | 1 M | Initial | 1-week | 2-week | 3-week | 1 M |
| Example 1 | pH | 10.42 | 10.43 | 10.45 | 10.43 | 10.36 | 10.42 | 10.36 | 10.34 | 10.4 | 10.32 |
| | Assay | 90.7 | 89.9 | 90.1 | 92.7 | 93.8 | 90.7 | 89.8 | 89.6 | 90.4 | 90.4 |
| Example 2 | pH | 10.51 | 10.54 | 10.55 | 10.54 | 10.5 | 10.51 | 10.5 | 10.48 | 10.48 | 10.47 |
| | Assay | 90.5 | 89.7 | 91.7 | 92.6 | 94.1 | 90.5 | 87.5 | 90.3 | 92.8 | 92 |
| Example 3 | pH | 10.59 | 10.57 | 10.63 | 10.6 | 10.56 | 10.59 | 10.6 | 10.56 | 10.53 | 10.54 |
| | Assay | 101.8 | 102.5 | 103.8 | 105 | 105.6 | 101.8 | 103 | 100.6 | 103.1 | 103.8 |
| Example 4 | pH | 11.55 | 11.78 | 11.96 | 11.95 | 12.14 | 11.55 | 11.84 | 11.81 | 11.82 | 12.13 |
| | Assay | 105.7 | 104.8 | 105.6 | 107.5 | 108.7 | 105.7 | 103.5 | 102.7 | 105 | 101.9 |
| Example 5 | pH | 10.62 | 10.6 | 10.64 | 10.65 | 10.58 | 10.62 | 10.6 | 10.55 | 10.6 | 10.58 |
| | Assay | 97.9 | 98.1 | 100.7 | 102 | 102.5 | 97.9 | 98.3 | 99.2 | 100.5 | 99.7 |
| Example 6 | pH | 10.2 | 10.22 | 10.26 | 10.24 | 10.19 | 10.2 | 10.23 | 10.23 | 10.24 | 10.19 |
| | Assay | 98.1 | 98 | 99.9 | 103.2 | 102.7 | 98.1 | 97.9 | 98.3 | 99.9 | 99.4 |
| Example 7 | pH | 10.11 | 10.12 | 10.07 | NA | 10.04 | 10.11 | 10.11 | 10.07 | NA | 10.06 |
| | Assay | 104.9 | 109 | 107.9 | NA | 105.2 | 104.9 | 108.2 | 106.3 | NA | 100.1 |
| Example 8 | pH | 10.06 | 10.06 | 10.02 | NA | 10 | 10.06 | 10.06 | 10.02 | NA | 10.02 |
| | Assay | 99.2 | 100.8 | 100.8 | NA | 98.3 | 99.2 | 99.7 | 98.5 | NA | 98.5 |
| Example 9 | pH | 10.72 | 11.19 | 11.95 | NA | 11.44 | 10.72 | 11.67 | 11.87 | NA | 11.27 |
| | Assay | 101.1 | 102.9 | 102.5 | NA | 99.9 | 101.1 | 102.1 | 101 | NA | 98 |
| Example 10 | pH | 10.46 | 10.44 | 10.41 | NA | 10.4 | 10.46 | 10.47 | 10.4 | NA | 10.39 |
| | Assay | 98.7 | 101.2 | 101.5 | NA | 98.4 | 98.7 | 101.1 | 99.6 | NA | 97.4 |

TABLE 2

| Formulation # | Storage Temperatures | | | | | | | | |
|---|---|---|---|---|---|---|---|---|---|
| | 40° C. | | | | | 25° C. | | | |
| Example 12 | Initial | 1 M | 2 M | 3 M | 6 M | 1 M | 2 M | 3 M | 6 M |
| Appearance | A clear colorless solution | A clear colorless solution | A clear colorless solution | A clear colorless solution | A clear colorless solution | A clear colorless solution | A clear colorless solution | A clear colorless solution | A clear colorless solution |
| pH | 10 | 10.1 | 10 | 10.2 | Not tested | 10.1 | 10 | 10.1 | Not tested |
| Assay | 99.30% | 99.20% | 96.90% | 96% | 95.10% | 99% | 98% | 96.80% | 97.20% |
| Total Impurities | 0.22% | 0.46% | 1.84% | 1.55% | 2.35% | 0.26% | 0.84% | 0.70% | 1.14% |

It was observed from stability studies that the formulations are stable and no significant increase in impurities were observed even at accelerated conditions.

The invention claimed is:

1. A ready-to-use liquid composition comprising levothyroxine or a pharmaceutically acceptable salt thereof, lysine at a concentration of about 1.4 mg/ml to about 1.5 mg/ml, and one or more pharmaceutically acceptable excipients, wherein the composition is devoid of tromethamine and lysine is the sole buffer in the composition.

2. The ready-to-use liquid composition of claim 1, wherein the levothyroxine or a pharmaceutically acceptable salt thereof is levothyroxine sodium.

3. The ready-to-use liquid composition of claim 2, wherein the concentration of levothyroxine sodium is about 20 μg/mL, about 40 μg/mL or about 100 μg/mL.

4. The ready-to-use liquid composition of claim 1, wherein the concentration of lysine is about 1.46 mg/ml.

5. The ready-to-use liquid composition of claim 1, wherein the one or more pharmaceutically acceptable excipients are selected from chelating agent, stabilizing agents, tonicity agents, pH adjusting agents, antioxidants, preservatives and water.

6. The ready-to-use liquid composition of claim 5, wherein the stabilizing agent is selected from sodium iodide, potassium iodide, and cyclodextrins and is present in a concentration of about 0.01 mg/mL to about 5 mg/mL.

7. The ready-to-use liquid composition of claim 1, wherein the composition has a pH of about 8.0 to 12.0.

8. The ready-to-use liquid composition of claim 1, wherein the composition is a solution filled in a vial, an ampoule, a bag, a bottle, a cartridge, or a syringe.

9. The ready-to-use liquid composition of claim 5, wherein the tonicity agent is selected from sodium chloride and glycerol.

10. The ready-to-use liquid composition of claim 1, wherein the composition is stable for at least 12 months at 25±2° C.

11. The ready-to-use liquid composition of claim 1, wherein the composition consists of:

| | |
|---|---|
| Levothyroxine sodium | 10 μg-1000 μg |
| Sodium iodide | 0.14 mg |
| Lysine | 1.46 mg |
| Sodium Chloride | 8.5 mg |
| NaOH and/or HCl | q.s. to adjust pH 6.0 to 9.0 |
| Water | 1 mL. |

12. The ready-to-use liquid composition of claim 1, wherein the composition consists of:

| | |
|---|---|
| Levothyroxine sodium | 10 μg-1000 μg |
| Sodium iodide | 0.14 mg |
| Lysine | 1.46 mg |
| Sulfobutylether-β-cyclodextrin | 80 mg |
| Sodium Chloride | 6.48 mg |
| NaOH and/or HCl | q.s. to adjust pH 6.0 to 9.0 |
| Water | 1 mL. |

13. The stable ready-to-use liquid composition of claim 2, comprising:
levothyroxine sodium in a concentration of about 20 μg/mL, about 40 μg/mL or about 100 μg/mL; and
a stabilizing agent selected from sodium iodide and potassium iodide in a concentration of about 0.01 mg/mL to about 5 mg/mL,
wherein the composition is devoid of tromethamine, and lysine is the sole buffer in the composition.

14. A method of treating myxedema coma in an individual in need thereof by administering the ready-to-use pharmaceutical composition of levothyroxine sodium of claim 2 to the individual, the method comprising:
providing the pharmaceutical composition of claim 2, wherein the pharmaceutical composition comprises levothyroxine sodium at a concentration of about 20 μg/mL, about 40 μg/mL or about 100 μg/mL and one or more pharmaceutical excipients other than tromethamine; and
injecting into the individual the pharmaceutical composition of claim 2 without adding any additional excipients to the pharmaceutical composition.

15. The method of claim 14, wherein the pharmaceutical composition consists of:

| | |
|---|---|
| Levothyroxine sodium | 10 μg-1000 μg |
| Sodium iodide | 0.14 mg |
| Lysine | 1.46 mg |
| Sodium Chloride | 8.5 mg |
| NaOH and/or HCl | q.s. to adjust pH 6.0 to 9.0 |
| Water | 1 mL. |

16. The method of claim 14, wherein the pharmaceutical composition consists of:

| | |
|---|---|
| Levothyroxine sodium | 10 μg-1000 μg |
| Sodium iodide | 0.14 mg |
| Lysine | 1.46 mg |
| Sulfobutylether-β-cyclodextrin | 80 mg |
| Sodium Chloride | 6.48 mg |

-continued

| NaOH and/or HCl | q.s. to adjust pH 6.0 to 9.0 |
| Water | 1 mL. |

17. The method of claim 14, wherein the composition is administered intravenously, subcutaneously or intramuscularly.

18. A liquid composition comprising levothyroxine or a pharmaceutically acceptable salt thereof, lysine at a concentration of about 0.1 mg/ml to about 7 mg/ml, and one or more pharmaceutically acceptable excipients, wherein the composition is devoid of tromethamine and lysine is the sole buffer in the composition and the composition is stable for at least 12 months at 25±2° C.

19. The liquid composition of claim 18, wherein the lysine is present at a concentration of about 1.4 mg/ml to about 1.5 mg/ml.

20. A method of treating myxedema coma in an individual in need thereof, the method comprising:
providing a pharmaceutical composition comprising (i) levothyroxine sodium at a concentration of about 20 μg/mL, about 40 μg/mL or about 100 μg/mL, (ii) lysine at a concentration of about 0.1 mg/ml to about 7 mg/ml, and (iii) one or more pharmaceutically acceptable excipients, wherein the composition is devoid of tromethamine and lysine is the sole buffer in the composition and the composition is stable for at least 12 months at 25±2° C., the method comprising; and
injecting the pharmaceutical composition into the individual without adding any additional excipients to the pharmaceutical composition.

\* \* \* \* \*